United States Patent
Hyeon et al.

(10) Patent No.: US 11,147,687 B2
(45) Date of Patent: Oct. 19, 2021

(54) CAGE FOR SPINAL SURGERY

(71) Applicant: Solco Biomedical Co., Ltd., Pyeongtaek-si (KR)

(72) Inventors: Mi-rim Hyeon, Hwaseong-si (KR); Hwi Geun Yu, Pyeongtaek-si (KR); Il Kim, Seoul (KR)

(73) Assignee: SOLCO BIOMEDICAL CO., LTD., Pyeongtaek-si (KR)

( * ) Notice: Subject to any disclaimer, the term of this patent is extended or adjusted under 35 U.S.C. 154(b) by 0 days.

(21) Appl. No.: 16/804,685

(22) Filed: Feb. 28, 2020

(65) Prior Publication Data
US 2021/0205091 A1 Jul. 8, 2021

(30) Foreign Application Priority Data
Jan. 2, 2020 (KR) .......................... 10-2020-0000469

(51) Int. Cl.
*A61F 2/44* (2006.01)
*A61F 2/30* (2006.01)

(52) U.S. Cl.
CPC ...... *A61F 2/447* (2013.01); *A61F 2002/3093* (2013.01); *A61F 2002/30563* (2013.01); *A61F 2002/30571* (2013.01); *A61F 2002/30784* (2013.01)

(58) Field of Classification Search
CPC .......... A61F 2/44; A61F 2/4455; A61F 2/446; A61F 2/4465; A61F 2/447; A61F 2002/448; A61F 2002/4485; A61F 2002/4495
See application file for complete search history.

(56) References Cited

U.S. PATENT DOCUMENTS

| | | | | |
|---|---|---|---|---|
| 6,136,031 A * | 10/2000 | Middleton | ............ | A61F 2/4465 623/17.16 |
| 7,208,222 B2 * | 4/2007 | Rolfe | ............ | A61F 2/442 428/304.4 |
| 7,828,847 B2 * | 11/2010 | Abdou | ............ | A61B 17/7014 623/17.13 |
| 8,172,902 B2 * | 5/2012 | Kapitan | ............ | A61F 2/4611 623/17.14 |

(Continued)

FOREIGN PATENT DOCUMENTS

| KR | 10-2007-0101239 | 10/2007 |
|---|---|---|
| KR | 10-2018-0115478 | 10/2018 |

OTHER PUBLICATIONS

Korean Office Action dated Jun. 18, 2021 for Korean Patent Application No. 10-2020-0000469, 4 pages.

*Primary Examiner* — Eric S Gibson
(74) *Attorney, Agent, or Firm* — Morgan, Lewis & Bockius LLP

(57) ABSTRACT

Provided is a cage for spinal surgery, in which an elastic structure having elasticity and a porous structure are combined with each other to elastically support the vertebra and increase a bone fusion rate.
The cage for the spinal surgery includes an elastic structure having a plurality of leaf springs provided, respectively, on both sides of a frame, one end of which protrudes, and a porous structure coupled to the elastic structure while being elastically supported by the elastic structure, and disposed in space between neighboring vertebrae, with a plurality of bone fusion holes for bone growth being formed on a surface of the porous structure.

6 Claims, 3 Drawing Sheets

(56) References Cited

U.S. PATENT DOCUMENTS

| | | | |
|---|---|---|---|
| 8,236,055 B2* | 8/2012 | Cordaro | A61F 2/4455 623/17.11 |
| 8,313,529 B2* | 11/2012 | Lechmann | A61F 2/4425 623/17.16 |
| 8,540,452 B2* | 9/2013 | Jimenez | A61F 2/4611 403/220 |
| 2005/0112397 A1* | 5/2005 | Rolfe | A61B 17/866 428/593 |
| 2005/0251260 A1* | 11/2005 | Gerber | A61F 2/4425 623/17.13 |
| 2006/0200243 A1* | 9/2006 | Rothman | A61F 2/442 623/17.13 |
| 2007/0032791 A1* | 2/2007 | Greenhalgh | A61B 17/8858 606/279 |
| 2007/0191958 A1* | 8/2007 | Abdou | A61B 17/7035 623/17.16 |
| 2007/0219634 A1* | 9/2007 | Greenhalgh | A61F 2/446 623/17.16 |
| 2008/0077246 A1* | 3/2008 | Fehling | A61F 2/442 623/17.16 |
| 2009/0118836 A1* | 5/2009 | Cordaro | A61F 2/442 623/17.16 |
| 2009/0157185 A1* | 6/2009 | Kim | A61F 2/442 623/17.16 |
| 2009/0222100 A1* | 9/2009 | Cipoletti | A61F 2/4611 623/17.16 |
| 2010/0016970 A1* | 1/2010 | Kapitan | A61F 2/4611 623/17.12 |
| 2010/0082109 A1* | 4/2010 | Greenhalgh | A61F 2/447 623/17.15 |
| 2010/0185291 A1* | 7/2010 | Jimenez | A61F 2/4611 623/17.16 |
| 2010/0209184 A1* | 8/2010 | Jimenez | F16F 1/025 403/291 |
| 2011/0029087 A1* | 2/2011 | Haider | A61F 2/442 623/17.16 |
| 2011/0112644 A1* | 5/2011 | Zilberstein | A61B 17/7079 623/17.15 |
| 2011/0208307 A1* | 8/2011 | Lechmann | A61F 2/4425 623/17.16 |
| 2017/0258606 A1* | 9/2017 | Afzal | A61F 2/4455 |
| 2020/0093612 A1* | 3/2020 | Blain | A61F 2/4601 |

* cited by examiner

CAGE FOR SPINAL SURGERY

CROSS REFERENCE TO RELATED APPLICATIONS

This application claims priority to Korean Patent Application No. KR 10-2020-0000469 filed Jan. 2, 2020, which is incorporated by reference herein in its entirety.

BACKGROUND OF THE DISCLOSURE

Field of the Invention

The present disclosure relates to an implant apparatus for spinal surgery placed on the spine.

Related Art

Generally, the spine is composed of 24 bones (excluding sacral spine), which are connected by joints called disks between the respective bones to support the spine and absorb shocks. Thereby, the spine can help to maintain the posture of the human, form the basis of movement, and play an important role in protecting internal organs.

However, if an abnormal posture is maintained for a long time, the spine suffers from degenerative diseases due to aging or is subjected to external shocks, the disk of the spinal joint may be damaged, thus resulting in spinal disk diseases. These spinal disk diseases compress nerves connected to respective parts of the human body via the spinal joints, thus causing pain.

Therefore, patients having the spinal disk diseases undergo the following procedure: a damaged disk is removed so that the nerve is not pressed or compressed, and a hollow cage made of metal or plastic materials is filled with bone chips to be inserted into a portion from which the disk has been removed.

Such a cage for the spinal surgery is a part where fusion with the vertebra is important. However, the conventional cage is problematic in that it is not fused with the vertebra well.

Furthermore, in the case of using a porous cage, it is easily fused with a peripheral osseous tissue, but is weak in strength for supporting the vertebra.

CITED REFERENCE

Patent Document (Patent Document 1) Korean Patent No. 10-1225006 (Title of Invention: Porous cage for intervertebral body fusion and the manufacturing method thereof, published on Jan. 22, 2013)

(Patent Document 2) Korean Patent Publication No. 10-2019-0134903 (Title of Invention: Cage for spinal fusion, laid open on Dec. 5, 2019)

SUMMARY OF THE INVENTION

The present disclosure provides a cage for spinal surgery in which an elastic structure having elasticity and a porous structure are combined with each other to elastically support the vertebra and increase a bone fusion rate.

In an aspect, a cage for spinal surgery may include an elastic structure having a plurality of leaf springs provided, respectively, on both sides of a frame, one end of which protrudes, and a porous structure coupled to the elastic structure while being elastically supported by the elastic structure, and disposed in space between neighboring vertebrae, with a plurality of bone fusion holes for bone growth being formed on a surface of the porous structure.

The elastic structure may be configured such that the leaf springs disposed outside the porous structure are vertically installed at regular intervals, thus supporting a load acting on the porous structure.

The frame may include a protrusion that is formed on a front portion thereof in an entry direction of the elastic structure, and a fixing hole that is formed in a rear portion of the frame to insert a spinal surgery apparatus therein.

The porous structure may include a bone insertion space that is defined to insert a bone graft therein, and a bone insertion hole that is formed in an upper portion of the bone insertion space to communicate with the bone insertion space.

A plurality of spikes may be formed along outer edges of upper and lower portions of the porous structure to fix the porous structure to the vertebra.

The elastic structure and the porous structure may be combined with each other to have a streamlined shape and have load resistance to elastically cope with an externally applied load.

The present disclosure provides a cage for spinal surgery which elastically supports the vertebra and increases a bone fusion rate through the cage made by combining an elastic structure with a porous structure, thus allowing a patient to quickly recover from surgery.

Furthermore, the present disclosure provides a cage for spinal surgery which improves the rigidity and the load resistance of the cage, thus preventing the cage from being broken and deformed.

DESCRIPTION OF EXEMPLARY EMBODIMENTS

Hereinafter, a cage for spinal surgery in accordance with an embodiment of the present disclosure will be described with reference to the accompanying drawings. The present disclosure is not limited or restricted by the embodiment. Further, in describing the present disclosure, specific details of known functions or configurations may be omitted to clarify the gist of the present disclosure.

Figure 1:
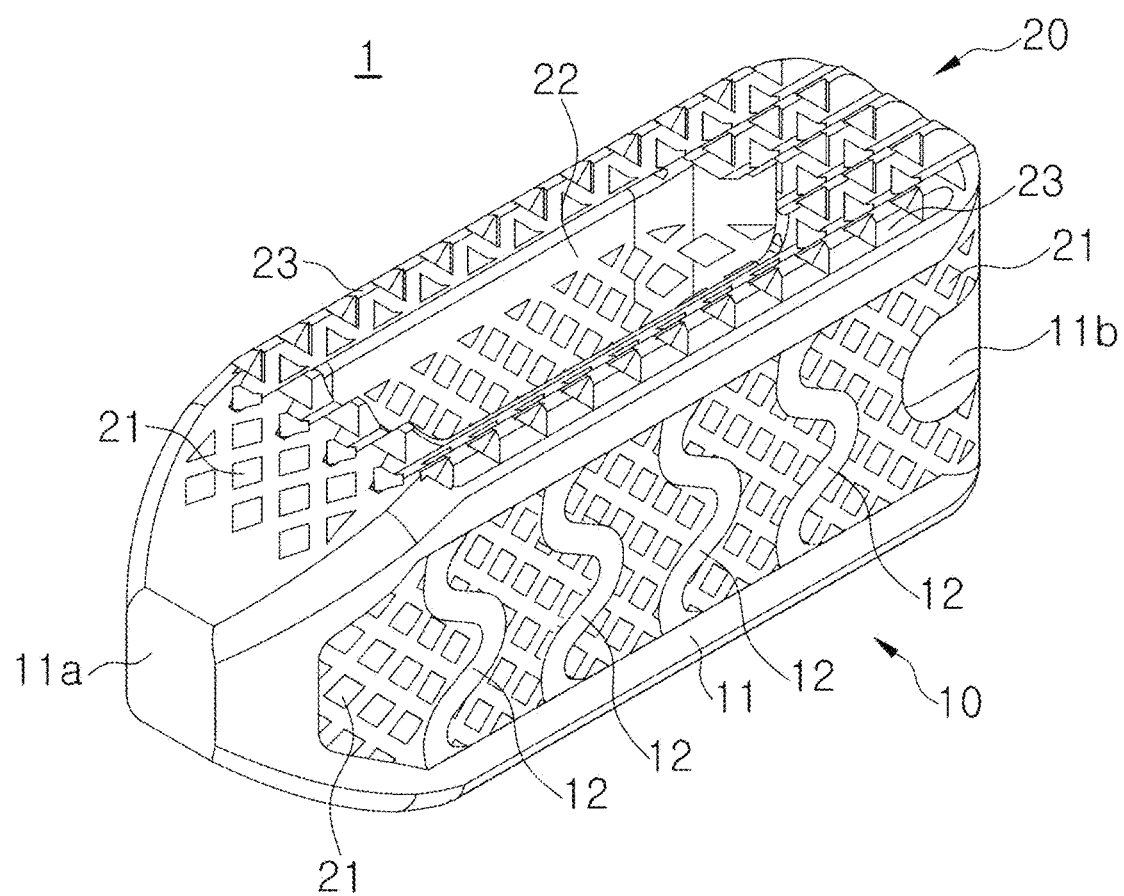
FIG. 1 is a diagram illustrating a cage for spinal surgery in accordance with an embodiment of the present disclosure.
Figure 2:
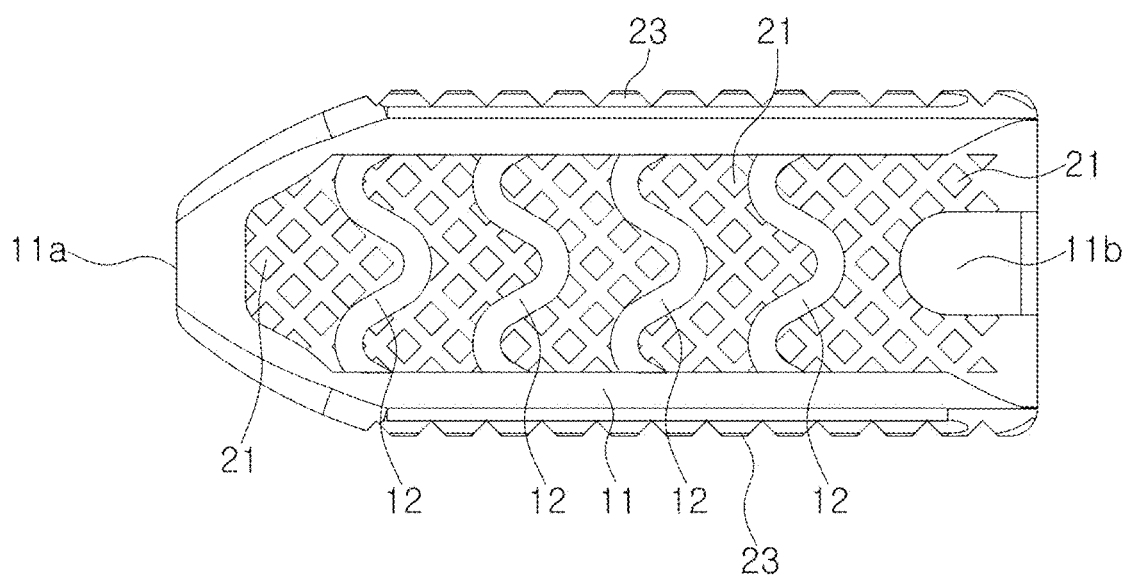
FIG. 2 is a diagram illustrating a side structure of the cage for the spinal surgery in accordance with the embodiment of the present disclosure.
Figure 3:
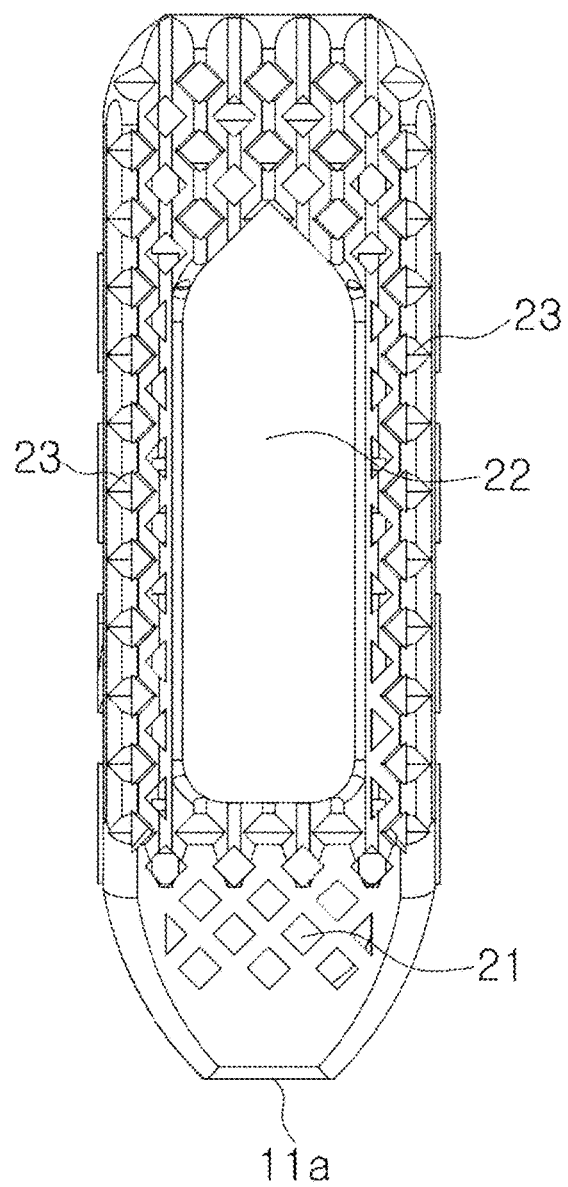
FIG. 3 is a diagram illustrating an upper structure of the cage for the spinal surgery in accordance with the embodiment of the present disclosure.

FIG. 1 is a diagram illustrating a cage for spinal surgery in accordance with an embodiment of the present disclosure. FIG. 2 is a diagram illustrating a side structure of the cage for the spinal surgery in accordance with the embodiment of the present disclosure. FIG. 3 is a diagram illustrating an upper structure of the cage for the spinal surgery in accordance with the embodiment of the present disclosure.

Referring to FIGS. 1 to 3, the cage 1 for the spinal surgery in accordance with the embodiment of the present disclosure is made by combining an elastic structure 10 and a porous structure 20. The elastic structure 10 may enhance the support force of the cage 1, and the porous structure 20 may enhance the bone fusion rate of the cage 1.

According to this embodiment, the elastic structure 10 of the cage 1 is configured such that a plurality of leaf springs 12 is provided, respectively, on both sides of a frame 11, one end of which protrudes. The elastic structure may elastically support a load acting on the elastic structure 10 using the leaf springs 12.

Furthermore, the porous structure 20 of the cage 1 is coupled to the elastic structure 10 while being elastically supported by the elastic structure 10. The porous structure is disposed in space between neighboring vertebrae, with a plurality of bone fusion holes 21 for bone growth being formed on a surface of the porous structure. The osseous tissue is attached to the plurality of bone fusion holes 21 formed in the porous structure 20 and then grows, and the surface of the porous structure 20 forms a mesh structure through the bone fusion holes 21.

That is, the cage 1 is made by combining the elastic structure 10 that has the elastic force with the porous structure 20 that may increase the bone fusion rate. The cage can exhibit the advantages of both the elastic structure 10 and the porous structure 20, thus maximizing the support force of the cage 1 and the bone fusion effect.

According to this embodiment, the elastic structure 10 is configured such that the leaf springs 12 disposed outside the porous structure 20 are vertically installed at regular intervals, thus supporting a load acting on the porous structure 20. The leaf springs 12 are disposed, respectively, on left and right sides of the frame 11. The leaf springs 12 of the same structure are disposed on the left and right sides of the elastic structure 10, thus allowing the cage 1 to have a uniform support force against a load.

Furthermore, the frame 11 has a protrusion 11a that is formed on a front portion thereof in the entry direction of the elastic structure 10, and a fixing hole 11b that is formed in a rear portion of the frame 11 to insert the spinal surgery apparatus therein. An end of the spinal surgery apparatus is inserted into the fixing hole 11b, so that the cage 1 may be fixedly inserted into a patient's spinal region. The protrusion 11a allows the cage 1 moving towards a surgical site to more easily enter the spinal region.

In this regard, the porous structure 20 may have a bone insertion space that is defined to insert a bone graft therein, and a bone insertion hole 22 communicating with the bone insertion space may be formed in an upper portion of the bone insertion space. The bone fusion occurs in the state where the bone inserted through the bone insertion hole 22 is filled in the bone insertion space.

A plurality of spikes 23 may be formed along outer edges of upper and lower portions of the porous structure 20 to fix it to the vertebra. The spikes 23 allow the porous structure 20 to have a frictional force, thus preventing the undesirable movement of the cage 1 that is fixed to the spinal region. Since the cage 1 is firmly fixed through the spikes 23, the bone fusion may more stably occur.

Hence, the cage 1 made by combining the elastic structure 10 and the porous structure 20 can increase the load resistance through the elastic structure 10, and can increase the bone fusion rate through the porous structure 20.

Figure 4:
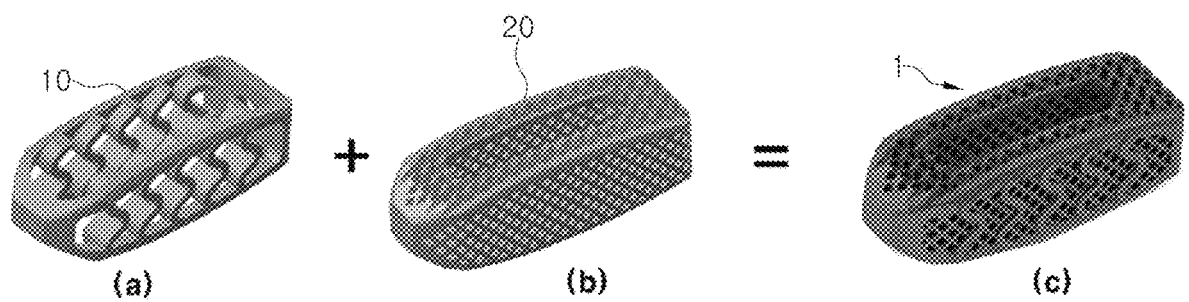
FIG. 4 is a diagram illustrating a configuration of the cage for the spinal surgery in accordance with the embodiment of the present disclosure.
Figure 5:
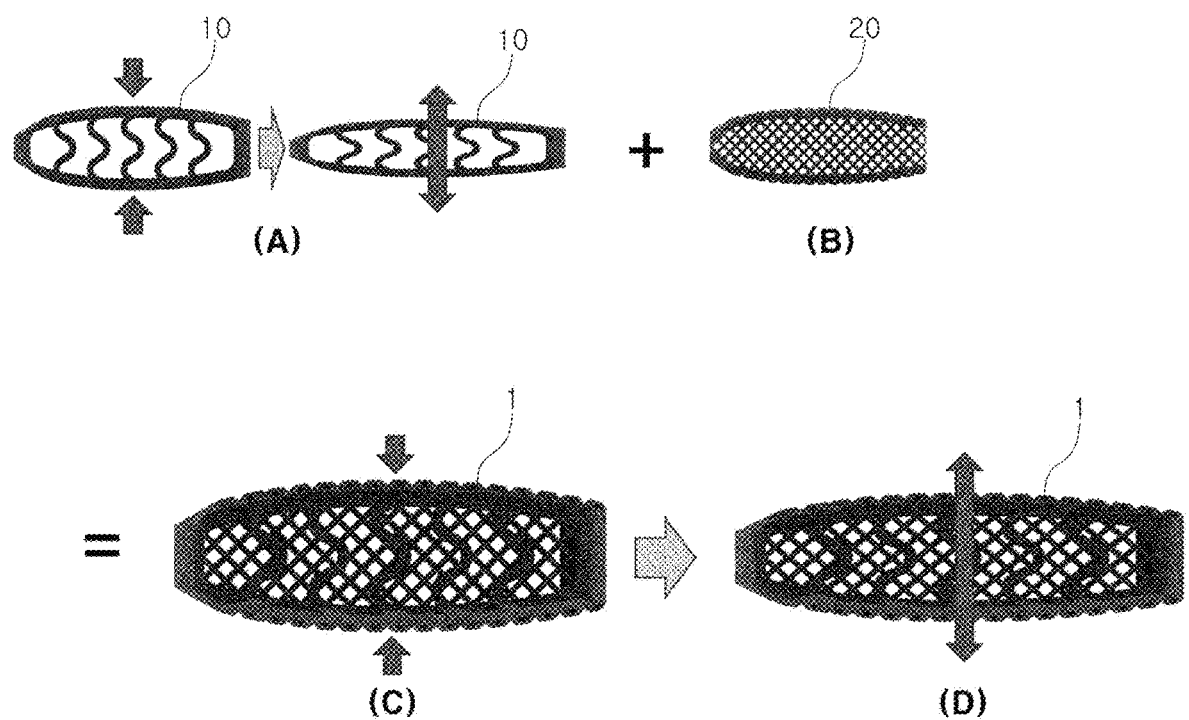
FIG. 5 is a diagram illustrating resistance to a load of the cage for the spinal surgery in accordance with the embodiment of the present disclosure.

FIG. 4 is a diagram illustrating a configuration of the cage for the spinal surgery in accordance with the embodiment of the present disclosure. FIG. 5 is a diagram illustrating resistance to a load of the cage for the spinal surgery in accordance with the embodiment of the present disclosure.

Referring to FIG. 4, (a) shows the elastic structure 10 having the plurality of leaf springs 12. The protrusion 11a is formed on the front portion of the frame 11 of the elastic structure 10, the fixing hole 11b is formed in the rear portion of the elastic structure 10, and the plurality of leaf springs 12 is disposed, respectively, on the left and right sides of the frame 11 at regular intervals. It is possible to elastically support a vertical load acting on the cage 1 through the leaf springs 12.

(b) shows the porous structure 20 having the plurality of bone fusion holes 21. Since the surface of the porous structure 20 has a mesh shape, the bone fusion can be further increased through the bone fusion holes 21.

Referring to FIG. 5, (A) shows a state in which the elastic structure 10 is subjected to a vertical load and then deformed, and (B) shows the porous structure 20 coupled to the elastic structure 10.

Thus, (C) shows a state in which a vertical load is applied to the cage 1 made by combining the elastic structure 10 and the porous structure 20, and (D) shows load resistance elastically acting against a load applied to the cage 1.

That is, the cage 1 can be more firmly supported with less deformation under the vertical load. The cage 1 can be improved in resistance to an external load while being kept stable.

Figure 6:
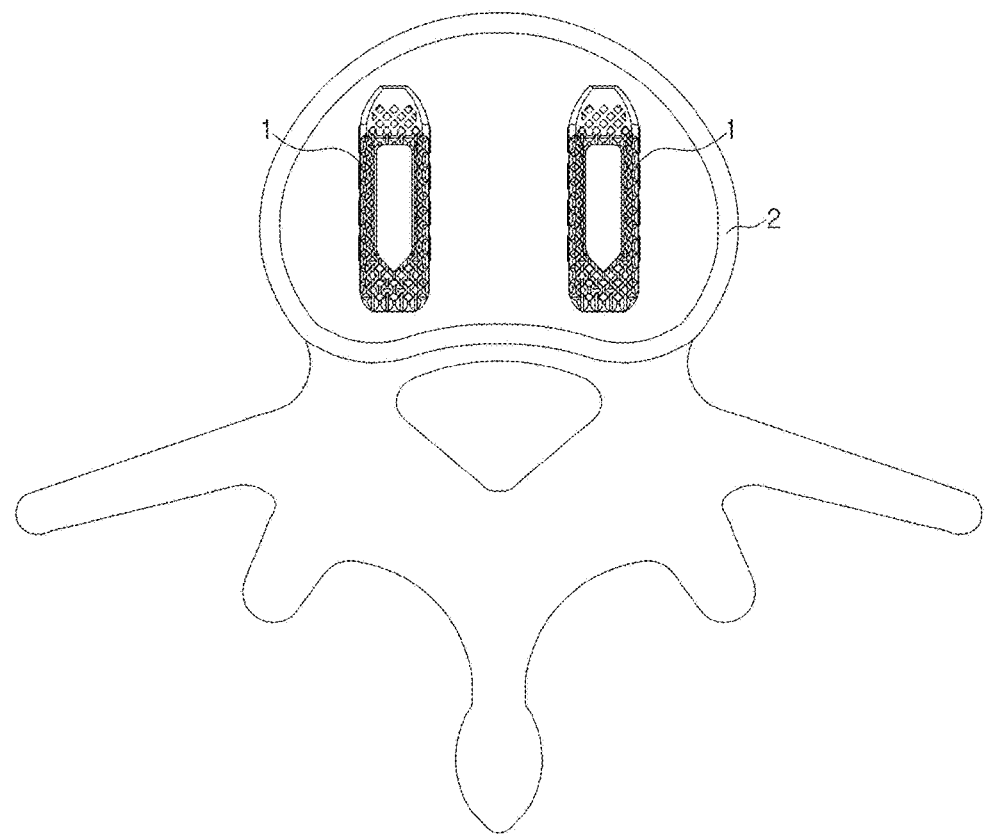
FIG. 6 is a diagram illustrating a state in which the cage for the spinal surgery in accordance with the embodiment of the present disclosure is placed in a space between vertebrae.

FIG. 6 is a diagram illustrating a state in which the cage for the spinal surgery in accordance with the embodiment of the present disclosure is placed in a space between vertebrae.

Referring to FIG. 6, the elastic structure 10 and the porous structure 20 are combined with each other to have a streamlined shape and have load resistance that elastically copes with an externally applied load.

A plurality of cages 1 for the spinal surgery is placed in the space between the vertebrae 2, so that the bone fusion is realized through the cage 1, and simultaneously it is possible to more stably cope with an externally applied load through the elastic force of the cage 1.

Therefore, the cage 1 made by combining the elastic structure 10 and the porous structure 20 can elastically support the vertebra 2, and increase the bone fusion rate, thus allowing a patient to quickly recover from surgery.

Furthermore, the rigidity and the load resistance of the cage 1 are improved, thus preventing the cage 1 from being broken and deformed.

Although the present disclosure has been shown and described with reference to preferred embodiments for illustrating the principle of the present disclosure, the present disclosure is not limited to the above-described configuration and operation. Rather, those skilled in the art will appreciate that many changes and modifications of the present disclosure may be made without departing from the spirit and scope of the appended claims.

What is claimed is:

1. A cage for spinal surgery, comprising:
    an elastic structure having a frame and a plurality of leaf springs respectively formed on both sides of the frame; and
    a porous structure coupled to the elastic structure while being elastically supported by the elastic structure, and configured to be disposed in a space between neighboring vertebrae, with a plurality of bone fusion holes for bone growth being formed on a surface of the porous structure.

2. The cage of claim 1, wherein the elastic structure is configured such that leaf springs disposed to face an outer surface of the porous structure are vertically installed at regular intervals, thus supporting a load acting on the porous structure.

3. The cage of claim 1, wherein the frame comprises a protrusion that is formed on a front portion thereof in an entry direction of the elastic structure, and a fixing hole that is formed in a rear portion of the frame to insert a spinal surgery apparatus therein.

4. The cage of claim 1, wherein the porous structure comprises a bone insertion space that is defined to insert a bone graft therein, and a bone insertion hole that is formed in an upper portion of the bone insertion space to communicate with the bone insertion space.

5. The cage of claim 1, wherein a plurality of spikes are formed along outer edges of upper and lower portions of the porous structure to fix the porous structure to the vertebra.

6. The cage of claim 1, wherein the elastic structure and the porous structure are combined with each other to have a streamlined shape and have load resistance to elastically cope with an externally applied load.

* * * * *